United States Patent [19]

Hsieh

[11] Patent Number: 5,301,108
[45] Date of Patent: Apr. 5, 1994

[54] COMPUTED TOMOGRAPHY SYSTEM WITH Z-AXIS CORRECTION

[75] Inventor: Jiang Hsieh, Waukesha, Wis.

[73] Assignee: General Electric Company, Milwaukee, Wis.

[21] Appl. No.: 12,167

[22] Filed: Feb. 1, 1993

[51] Int. Cl.$^5$ .............................................. G06F 15/00
[52] U.S. Cl. ........................ 364/413.19; 364/413.14; 364/413.15; 364/413.16; 378/8
[58] Field of Search ............... 364/413.13, 413.14, 364/413.15, 413.16, 413.19; 378/8, 207; 382/6

[56] References Cited

U.S. PATENT DOCUMENTS

| 5,065,436 | 11/1991 | Matsumura | 364/413.19 |
|---|---|---|---|
| 5,218,533 | 6/1993 | Schanen | 364/413.15 |
| 5,222,021 | 6/1993 | Feldman et al. | 364/413.15 |
| 5,249,123 | 9/1993 | Hsieh | 364/413.19 |

*Primary Examiner*—Roy N. Envall, Jr.
*Assistant Examiner*—Frantzy Poinvil
*Attorney, Agent, or Firm*—Quarles & Brady

[57] ABSTRACT

An x-ray CT scanner is operated in a calibration procedure to produce error signature vectors that indicate detector elements that have a non-uniform response along the z-axis and which may generate ring or band artifacts when certain anatomies are scanned. A correction process employs these error signatures during the scan to determine when correction is necessary and to make those corrections to the projection data as it is acquired.

8 Claims, 7 Drawing Sheets

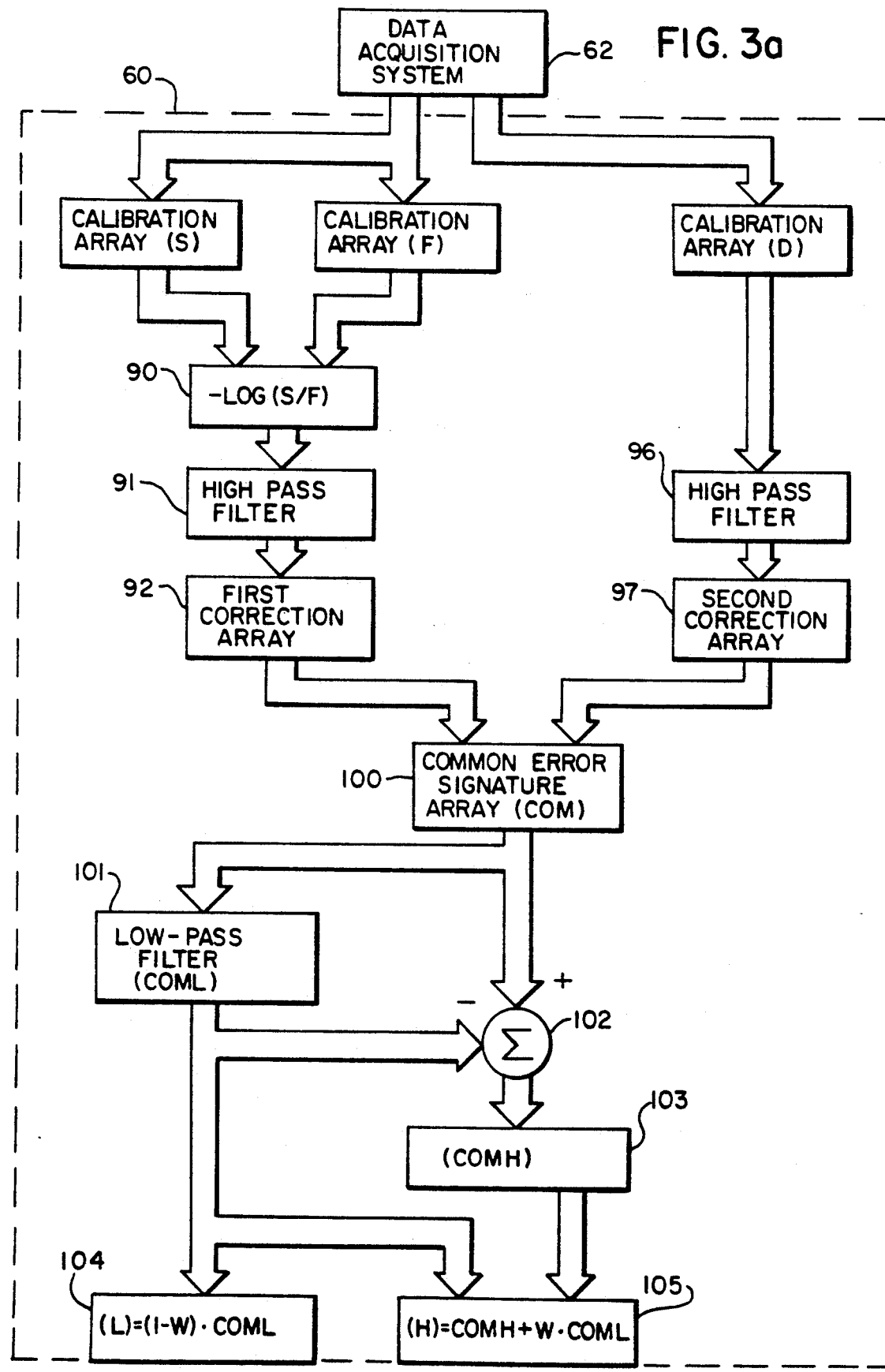

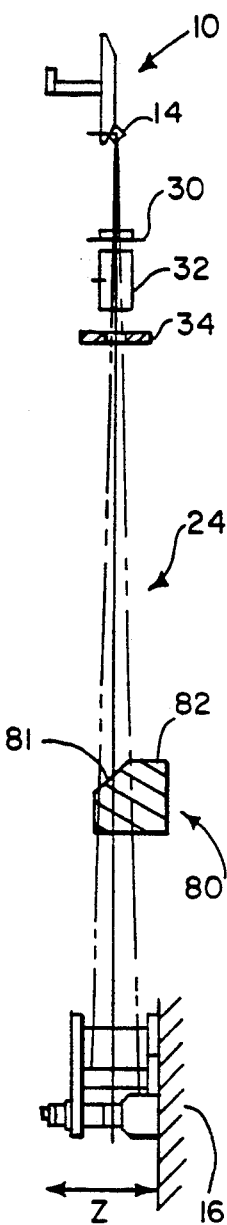
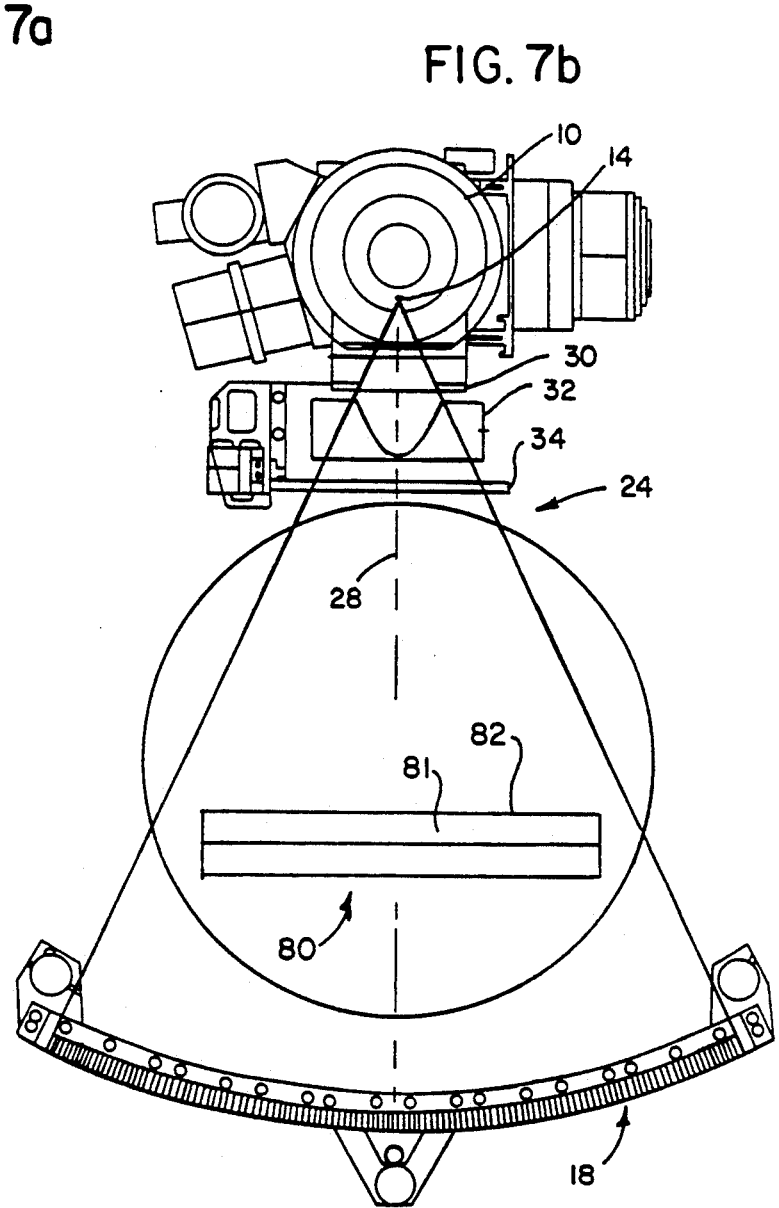
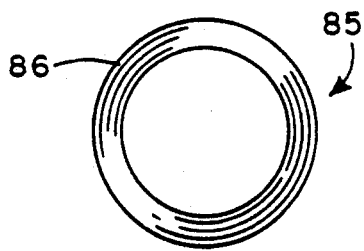
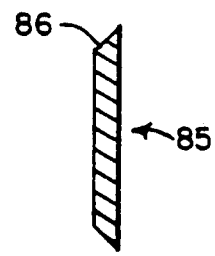
FIG. 7a FIG. 7b
FIG. 8a FIG. 8b

COMPUTED TOMOGRAPHY SYSTEM WITH Z-AXIS CORRECTION

BACKGROUND OF THE INVENTION

This invention relates to computed tomography equipment and specifically to the correction of errors caused by variations in x-ray detector sensitivity along the z-axis.

Computed tomography (CT) systems, include an x-ray source collimated to form a fan beam, the fan beam extending generally along a fan beam plane and directed through an object to be imaged. After passing through the imaged object, the fan beam is received by an x-ray detector array extending along the fan beam plane. The x-ray source and detector array are rotated together on a gantry within an imaging plane, generally parallel to the fan beam plane, around the image object.

The axis of rotation of the gantry is designated as the z-axis of the Cartesian coordinate system and the fan beam plane and imaging plane is parallel to the x-y plane of the coordinate system.

The detector array is comprised of detector cells each of which measures the intensity of transmitted radiation along a ray from the x-ray source to that particular detector cell. At each gantry angle, a projection is acquired comprised of intensity signals from each of the detector cells. The gantry is then rotated to a new gantry angle and the process is repeated to collect a number of projections along a number of gantry angles to form a tomographic projection set.

Each tomographic projection set is stored in numerical form for later computer processing to "reconstruct" a cross sectional image according to algorithms known in the art. The reconstructed image may be displayed on a conventional CRT or may be converted to a film record by means of a computer driven camera.

Ideally, the fan beam plane will strike the center line of the detector array. In practice, however, the fan beam plane may be displaced along the z-axis from the center line because of two effects. The first effect is the thermal expansion of the x-ray tube's anode and its support. The surface temperature of the tube's anode may rise as high as 2000° C. and the anode supporting structure may rise to 400° C. or more. This heating and the resulting expansion of the tube's anode and its support causes a shifting of the focal spot of the tube which moves the point from which the x-rays emanate. The shifting of the focal spot causes a corresponding shift in the fan beam plane.

The second effect is the mechanical deflection of the gantry and anode support as the gantry rotates. This deforming stress results from the changing angle of gravitational acceleration and the changing magnitude of centripetal acceleration as a function of the rotational velocity of the gantry, acting both on the gantry and anode.

Displacement of the fan beam plane along the z-axis of the detector array is a problem because it causes variations in detector signals that are "exogenous" or unrelated to the internal structure of the imaged object. Generally each detector cell's sensitivity to x-rays will be a function of the z-axis position of the fan beam along the surface of that cell, that is, the detector cells exhibit a non-uniform "z-axis sensitivity". This z-axis sensitivity, combined with motion of the fan beam plane on the detectors, produces the undesired variations in the strength of the detector signal. Such exogenous variations in the detector signals produce undesirable ring like artifacts in the reconstructed image.

Compounding the problem of correcting for variations in z-axis sensitivity is the fact that the z-axis sensitivity generally differs among different detector cells in the detector array. This difference will be termed "intercell sensitivity variation".

Displacement of the fan beam plane and thus variations in the detector signals may be predicted and corrected. In U.S. Pat. No 4,991,189, issued Feb. 5, 1991, assigned to the same assignee as the present invention, and incorporated by reference, a control system using a movable collimator adjusts the z-axis position of the fan beam plane as deduced from a pair of special detector cells. The special detector cells provide information to a computer model of the system which in turn is used to control the collimator and to correct the placement of the fan beam plane. While such closed loop controls of the fan beam location reduce z-axis artifacts, they do not eliminate the problem.

Intercell sensitivity can be corrected using data from a calibration scan performed before a patient is in place. However, such corrections do not eliminate ring and band artifacts due to variations in detector sensitivity along the z-axis. Consider, for example, the z-axis sensitivity profiles of three different detector cells #1-3 in FIGS. 4(a)–4(c). Detector cell #1 represents a perfect sensitivity profile, while detector cells #2 and #3 represent actual sensitivity profiles with different characteristics. If these three detector cells are exposed to an x-ray flux which is uniform, the detector responses will differ because of the different z-axis sensitivities profiles, but these can be corrected using the calibration data.

Consider, however, the situation in which the x-ray flux is not uniform along the z-axis, but is instead variably attenuated by the patient being imaged. One such x-ray flux density profile is shown in FIG. 5(a), and the resulting response of these three detector cells after air calibration in FIG. 4 are shown in FIG. 5(b). On the other hand, consider a different x-ray flux density profile as shown in FIG. 6(a) and the resulting response of the same three detector cells after air calibration in FIG. 6(b). It is apparent that the corrections needed to level the detector responses is a function of the x-ray flux density profile, which in turn is a function of the attenuation characteristics of the object being imaged. In other words, the corrections needed depend on the object being imaged, and calibration data acquired with no object present will not suffice to eliminate ring and band artifacts caused by variations in the z-axis sensitivity of detector cells.

SUMMARY OF THE INVENTION

The present invention related to a method for correcting projection profile data for errors caused by variations in the z-axis sensitivity of detector elements and z-axis x-ray flux gradients produced by the patient being scanned. More specifically, the invention includes the acquisition of x-ray attenuation data using a phantom that produces a non-uniform z-axis gradient in the x-ray flux producing an error signature vector that indicates by its values the variations expected in projection profile data when error conditions are present, comparing the error signature vector with each projection profile acquired during a scan of a patient to detect when error conditions are present, calculating correction values for the projection profile when error conditions are detected and applying the correction values to the projection profile.

A general object of the invention is to correct z-axis sensitivity errors which are introduced into the acquired x-ray attenuation profile when the structures through which the x-ray beam travels introduces a z-axis gradient in the x-ray flux density. Such object dependent errors cannot be corrected using conventional calibration techniques in which correction values are determined directly from a reference scan through air or a phantom. Instead, the reference scan according to the present invention produces an error signature vector that indicates what the x-ray attenuation profile is likely to look like when the error conditions exist. In other words, some scans will be conducted in which the requisite z-axis gradient conditions are not present and no corrections are required, whereas in other scans (for example, the head, liver and heart) significant corrections may be required to remove ring and band artifacts caused by non-uniform detector element response. Once the error condition is detected, then corrective values can be calculated using the error signature values, the x-ray attenuation profile values or a combination of both.

A more specific object of the invention is to correct for data-dependant errors as the projection data is being acquired. Each projection profile can be examined, and if required corrected, prior to its use in reconstructing an image. The resulting increase in reconstruction time is not significant and no further processing is required after image reconstruction.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 3(a) is a block diagram showing the processing of the calibration data acquired by the CT system of FIG. 2 according to the present invention;

FIGS. 7(a)-(b) are partial pictoral views of the CT scanner of FIG. 1 showing a rod calibration phantom in place;

FIGS. 8(a)-(b) are plan view and a view in cross section respectively of a disc calibration phantom which is also used in the CT scanner of FIG. 1;

DESCRIPTION OF THE PREFERRED EMBODIMENT

Figures 1A, 1B:
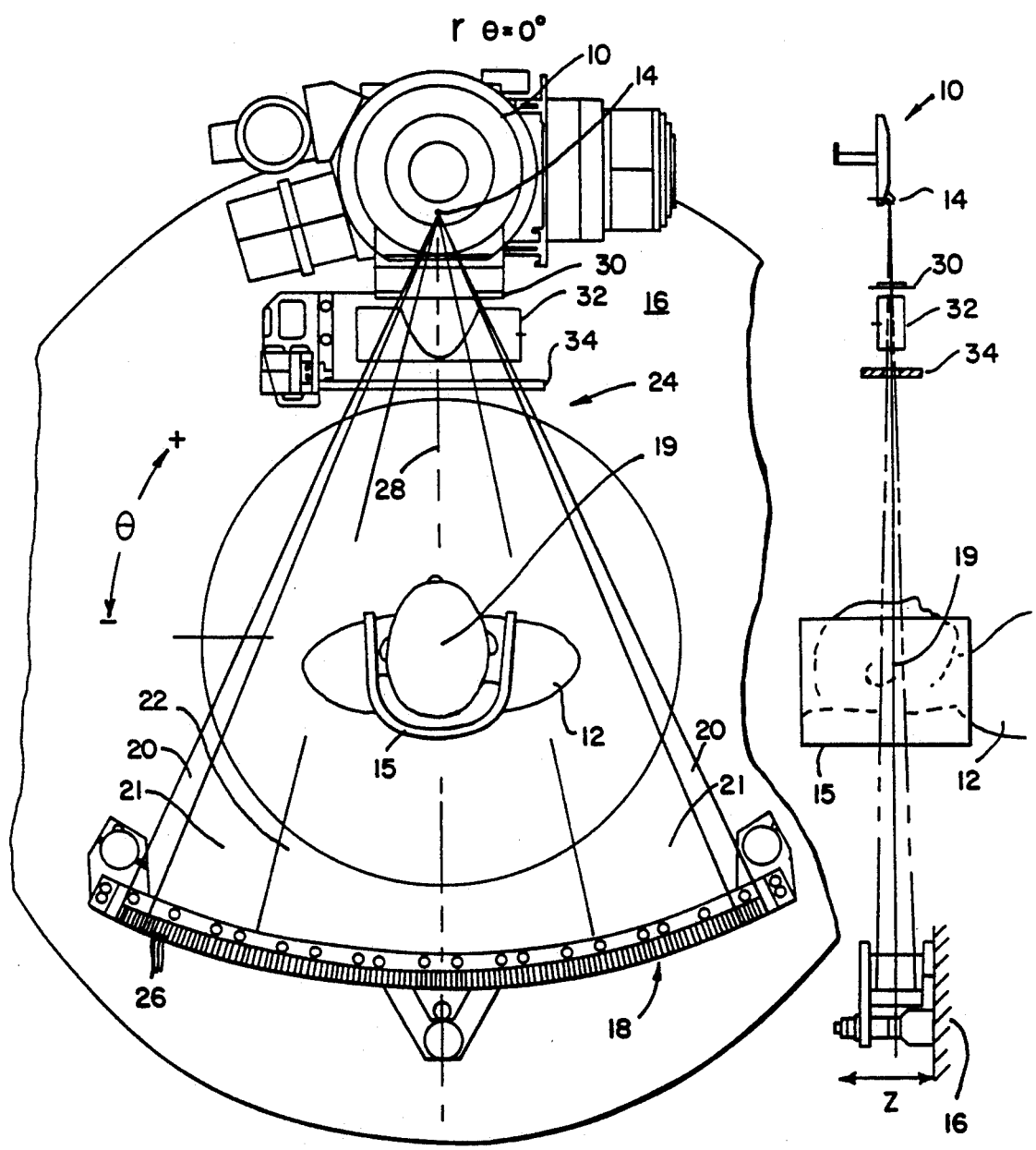
FIGS. 1(a)-(b) are front and side views, in elevation, of a CT gantry showing the relative positions of an x-ray source, detector array and fan beam about a patient's head.

Referring to FIG. 1, a CT gantry 16 representative of that used with a "third generation" CT scanner, holds an x-ray source 10 producing a fan beam of x-ray 24. The fan beam 24 is directed through a patient 12, positioned near a center 19 of the gantry 16, to be received by a detector array 18 also attached to the gantry 16. The patient's head is supported by a headholder 15.

The gantry 16 rotates within an x-y plane of a Cartesian coordinate system, termed the imaging plane, which is generally the same plane as that of the fan beam 24.

The detector array 18 is comprised of a number of detector elements or "channels" 26 positioned adjacent to each other within the imaging plane to subtend the fan beam 24. The channels 26 receive and detect radiation passing from the x-ray source 10, to produce a plurality of channel signals each associated with a particular channel 26. At a given orientation of gantry 16 about patient 12, signals for approximately 800 channels may be acquired, representing a detailed picture of the line integral of the attenuation of the fan beam 24 by the patient 12 at that angle. A gantry angle of zero is defined as that angle where a principle ray 28, centered in the fan beam 24, is directed vertically downward from the x-ray source 10.

The x-rays of the fan beam 24, immediately after leaving x-ray source 10 and prior to being received by the detector array 18, are filtered by a spectral filter 30 which filters out the lower energy x-rays from the fan beam 24. The fan beam 24 then passes through a bow tie filter 32 having a profile that produces an attenuation in the fan beam 24 complementing that which would be produced by a cylinder of water placed at the center 19 of the gantry 16. The purpose of the bow tie filter 32 is to reduce the range of intensity values received by the detector channels 26 for a typical patient 12 and hence to allow for an increase in sensitivity of the detector array 18 and its associated circuitry.

The bow tie filter 32 is followed by an aperture 34 which forms fan beam 24 and may be used to correct the position of the fan beam 24 with respect to the surface of the detector array 18 as described generally in U.S. Pat. No. 5,054,041 issued to the same assignee as that of the present application and incorporated herein by reference.

For a given patient 12, the channels 26 may be roughly divided into three groups: reference, over-range, and in range. Reference channels 20 of the detector array 18 are those intended not to be occluded by the patient 12 or headholder 15 and may serve the function of calibrating the projection data for variations in the x-ray flux from x-ray source 10, and serve further to permit automatic alignment of the fan beam 24 on the detector array 18. Over-range channels 21 of the detector array 18 are those channels within a given projection which, although possibly occluded by the imaged object 12, generally receive x-rays having so little attenuation that the ADC, used to digitize the signals of these channels, is over-ranged. And finally, in range channels 22 of the detector array 18, are those in a given projection which are sufficiently attenuated by the imaged object 12 so as not to over-range the ADC used to digitize the signals from these channels.

Figure 2:
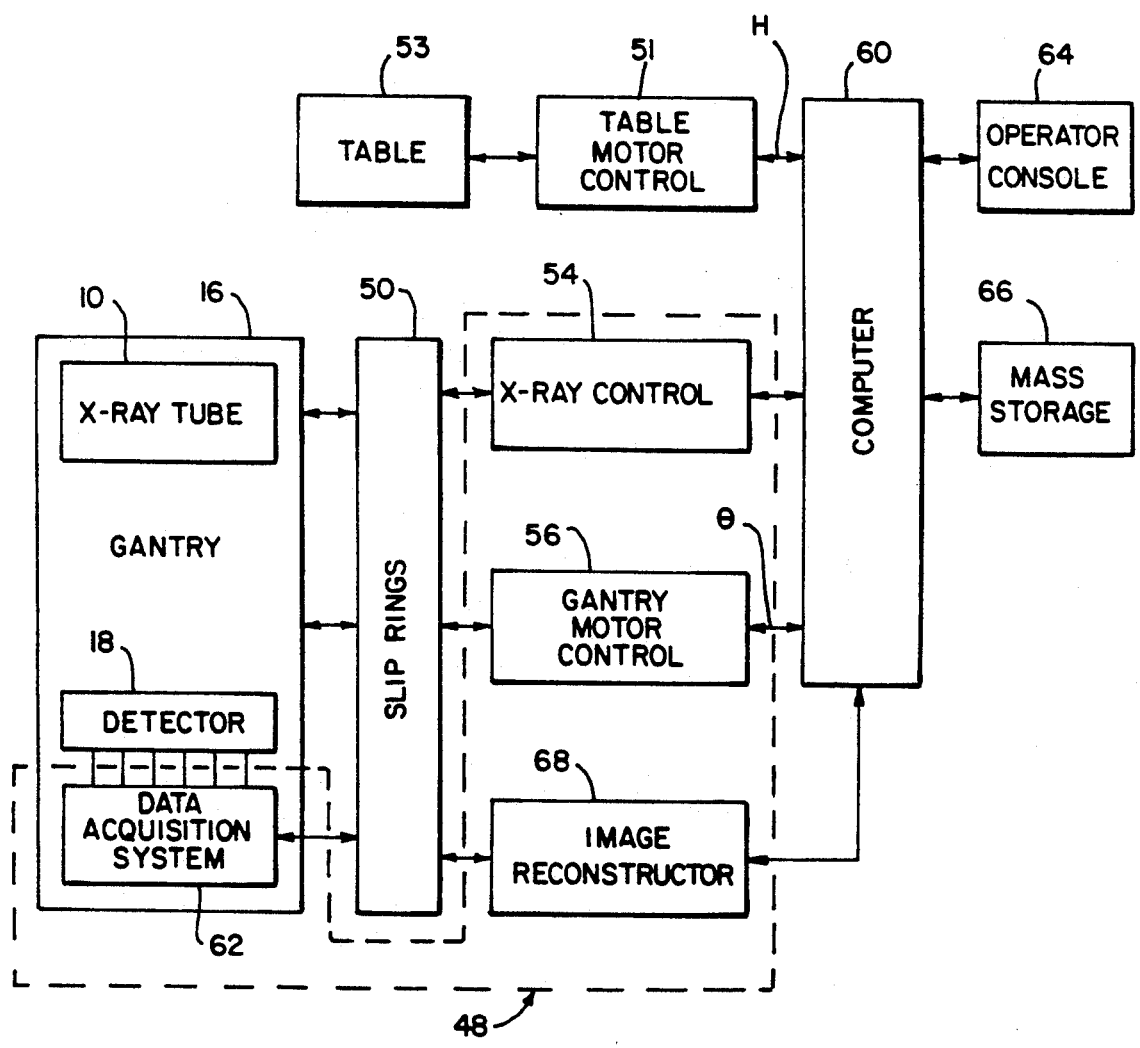
FIG. 2 is a block diagram of a CT control system associated with the gantry of FIG. 1 and useful for practicing the present invention.

Referring to FIG. 2, control circuitry for a CT imaging system suitable for use with the present invention includes a number of functional blocks 48. A data acquisition system 62 is connected to the detector array 18 and comprises a sampling means (not shown) for sampling the signals from each of the channels 26. An analog to digital converter ("ADC") (not shown) converts the sampled analog signals from each sampled channel 26 to a digital value for processing by later circuitry.

A radiotranslucent table 53 supports the patient 12 and the headholder 15, the latter which is typically fixed to the table 53. The table 53 may be moved through the image plane to align the slice of interest of the patient with the image plane, and may be raised or lowered to center the patient 12 within the opening of the gantry 16. The movement of the table is accomplished by motors (not shown) controlled by table motor control 51. The table motor control 51 also generates a value H indicating the height of table 53 with respect to the isocenter 19.

An x-ray control 54 provides power and timing signals to the x-ray source 10 with regard to the position of gantry 16 to acquire the projections. Gantry motor controller 56 controls the rotational speed and position of the gantry 16 and provides gantry angle information $\theta$ to the DAS 62 and the x-ray control 54 to permit accurate timing of the projections.

The image reconstructor 68 is a special purpose computer, such as an array processor, capable of very rapid parallel processing or "pipelining" as is necessary to produce images from the large amount of projection data. Array processors suitable for use as the image reconstructor 68 are commercially available from a variety of sources. The image reconstructor 68 receives the sampled and digitized signals from the channels 26 of the detector array 18 via the DAS 62 to perform high speed image reconstruction according to methods known in the art.

A computer 60 coordinates the operation of the DAS 62, the table motor control, the x-ray control 54, and the gantry motor control 56 and works in conjunction with image reconstructor 68 to reconstruct tomographic images from the set of projections acquired by the scanning process. The computer 60 receives commands and scanning parameters via operator console 64 which is generally a CRT display and keyboard which allows the operator to enter parameters for the scan and to display the reconstructed slice images and other information from the computer 60. A mass storage device 66 provides a means for storing operating programs for the CT imaging system, as well as image data for future reference by the operator.

Each of the above elements is connected to its associated elements on the gantry 16 via slip rings 50 to permit continuous rotation of the gantry 16.

The present invention is implemented in the CT system of FIG. 2 by first acquiring calibration data using specially designed phantoms described below and shown in FIGS. 7 and 8. This calibration data is then used to correct the attenuation profile data acquired during a normal scan of a patient. As will be described in more detail below with reference to FIG. 3(a), the calibration data acquisition is performed under the direction of a program executed by the computer 60 and two error signature vectors are produced. These are down loaded from the computer 60 to the image reconstructor 68 for use during subsequent scans. As will be described in more detail below with reference to FIG. 3(b), the image reconstructor 68 uses these error signature vectors during a normal scan to correct attenuation data profiles as they are acquired and prior to their use in reconstructing an image.

Referring particularly to FIGS. 3(a) and 7, the computer 60 directs the CT system to acquire three sets of calibration data. During the first acquisition, a shaped rod 80 made of an acrylic plastic such as that sold under the trademark PLEXIGLASS is placed in the field of view of the scanner and 984 sets of attenuation data are acquired with the gantry held stationary. As shown in FIG. 7(a), one surface 81 on the rod 80 is sloped at an angle of 25° with respect to the impinging x-ray flux, and the surface 81 is long enough and wide enough to intercept the entire 10 mm thick fan beam which impinges on the central 180 channels of the detector array 18. This produces a z-axis gradient in the x-ray flux density of the detected fan beam 24, and the resulting 984 signals from the central 180 detector elements are averaged and stored as a 180 element calibration array (S). None of the normal preprocessor corrections except offset corrections are made to these signals.

The rod 80 is then moved such that a surface 82 that is orthogonal to the plane of the fan beam 24 intercepts the entire fan beam 24 impinging on the central 180 detector elements. The uniform rod thickness through which the fan beam 24 passes during this acquisition attenuates the x-ray fan beam uniformly along the z-axis. The gantry remains stationary and 984 acquisition are obtained and averaged. The resulting averaged signals from the central 180 detector elements are stored as a calibration array (F). Again, none of the corrections normally performed in the preprocessor except offset corrections are made to these values.

The final calibration measurement is made with a different phantom in place. This disc-shaped phantom 85 is made of an acrylic plastic and is shown in FIGS. 8(a) and 8(b). It is placed at the isocenter of the scanner such that it intercepts the fan beam 24 impinging on the central 36 elements of the detector array 18 at all gantry positions. The circular edge 86 of the disc 85 is tapered at an angle of 57.5° with respect to the plane of the fan beam 24 and the disc 85. The disc phantom 85 is thick enough to intercept the entire thickness of the fan beam 24, and as a result, the x-ray flux impinging on the central 36 detector elements has a z-axis gradient in its flux density. The data is acquired in the normal manner by revolving the gantry and obtaining 984 separate views which are averaged together to form a single 36 element calibration array (D). In this case the usual preprocessing such as beam hardening correction, offset correction, system gain corrections and logarithm calculations are performed on each acquisition before averaging.

Referring particularly to FIG. 3(a), the three calibration arrays (S), (F) and (D) are processed off-line to produce two error signature vectors (L) and (H) which are used during subsequent patient scans. As indicated at block 90, the logarithm of the ratio of the elements in the (S) array and the (F) array are calculated to produce a 180 element array which contains variations caused by the combined effect of non-uniform z-axis response of detector elements and a z-axis gradient in the x-ray flux density. However, this data also contains low frequency variations caused by geometric errors (i.e. imperfect alignment of the rod phantom 80) which are filtered out by a high pass filter 91. The filter 91 operates by first calculating a second order polynomial which best fits the array of data input to the filter. A conventional polynomial fit function is used for this purpose. The values in the second order polynomial are then subtracted from the corresponding elements in the input array to remove the low frequency geometric fluctuations therein. The result is a 180 element first correction array stored at 92.

The calibration array (D) is processed somewhat differently because it has been preprocessed and indicates the line integral of the x-ray attenuations. However, the low frequency fluctuations caused by the geometry of the phantom 85 must be removed by a high pass filter 96 and the resulting 36 element "second correction array" is stored at block 97. The high pass filter 96 operates by fitting a second order polynomial to the 21 input data elements centered around the data element being filtered. The data element is replaced with the corresponding point in the polynomial and the process is repeated for each of the 36 input data elements.

As indicated at process block 100 in FIG. 3(a), the two correction arrays 92 and 97 are combined to form a 180 element common error signature array (COM). The central 36 elements of the common array (COM) are formed as follows: if the corresponding elements of the first and second correction arrays 92 and 97 have the opposite sign, use the value from the second correction array 97; or if they have the same sign, use the value with the larger magnitude. The common error signature array (COM) indicates the errors which are likely to be introduced by the central 180 detector elements due to non-uniform z-axis response to impinging x-rays.

The image artifacts introduced by non-uniform detectors may be manifested as a ring caused by a single detector element, or an entire block of detector elements may produce a band artifact. The first artifact is revealed by high frequency variations in the error signature array (COM) and the second artifact is revealed by low frequency variations. High frequency errors can be corrected on a channel-by-channel basis, whereas low frequency errors are corrected by changing the response of a group of channels, since the detection of such an error in one channel indicates errors in the adjacent channels. Accordingly, the common error signature (COM) is split into two arrays and these are used separately to correct the two types of errors.

Figure 9:
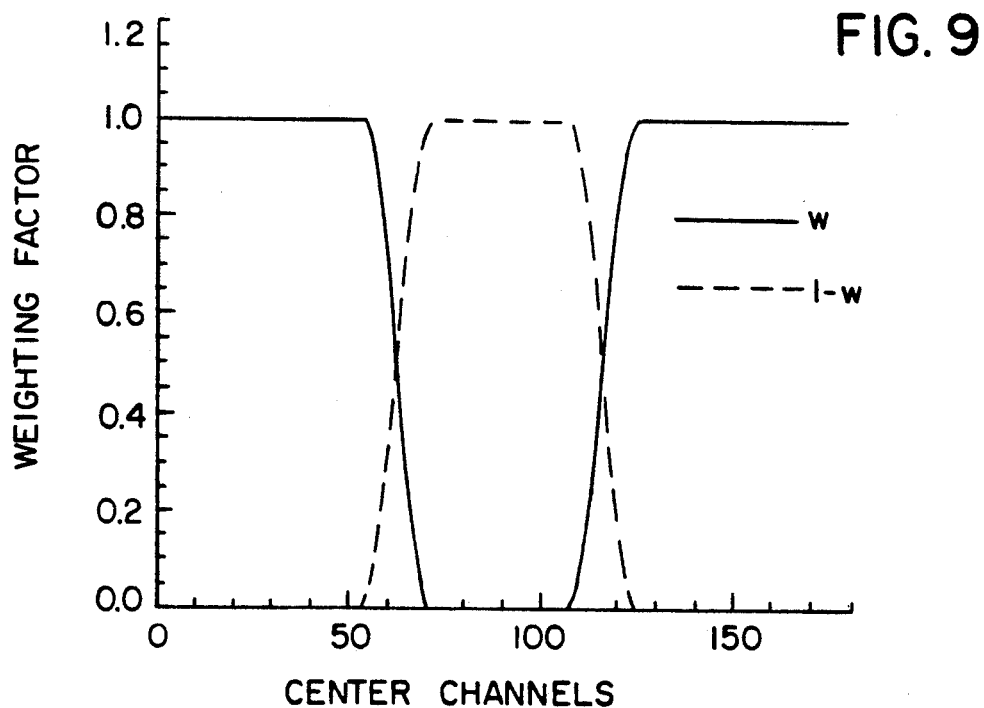
FIG. 9 is a graphic representation of a weighting factor W employed in the process of FIG. 3(a)

Referring still to FIG. 3(a), the common error signature (COM) is applied to a low-pass filter at process block 101 to produce a 180 element low frequency array (COM-L) that reveals errors caused by blocks of adjacent detector elements (i.e. band artifacts). This array COM-L is then subtracted from the common error signature (COM) at a summing point 102 to produce a 180 element high frequency array (COM-H) at 103 that reveals errors caused by single detector elements 1 (i.e. ring artifacts). The low pass filter 101 used in a Gausian filter (9 points) with $\sigma=1.22$. Low frequency corrections are made only to the 36 center channels where band artifacts are most troublesome. The sensitivity to errors decreases quickly as one moves away from the center channels, due to the nature of the reconstruction algorithm. Since it is important to avoid abrupt changes in the reconstruction process, two error signatures (L and H) are formed by the weighted sum of the low frequency and high frequency arrays COML and COMH:

$$L=(1-W)(COML)$$

$$H=(COMH)+W(COML)$$

where W is a weighting factor that is different for each channel as shown in FIG. 9. The low frequency error signature (L) is produced at process block 104 and it contains only the low frequency error information for the inner $\approx 36$ channels. The high frequency error signature (H) is produced at process block 105 and it contains both high frequency and low frequency error information for the outer ones of the central 180 detector channels and the high frequency error information for the inner $\approx 36$ detector channels. These two error signature arrays (L) and (H) are downloaded to the image reconstructor 68 for use during a patient scan as will now be described.

Figure 3B:
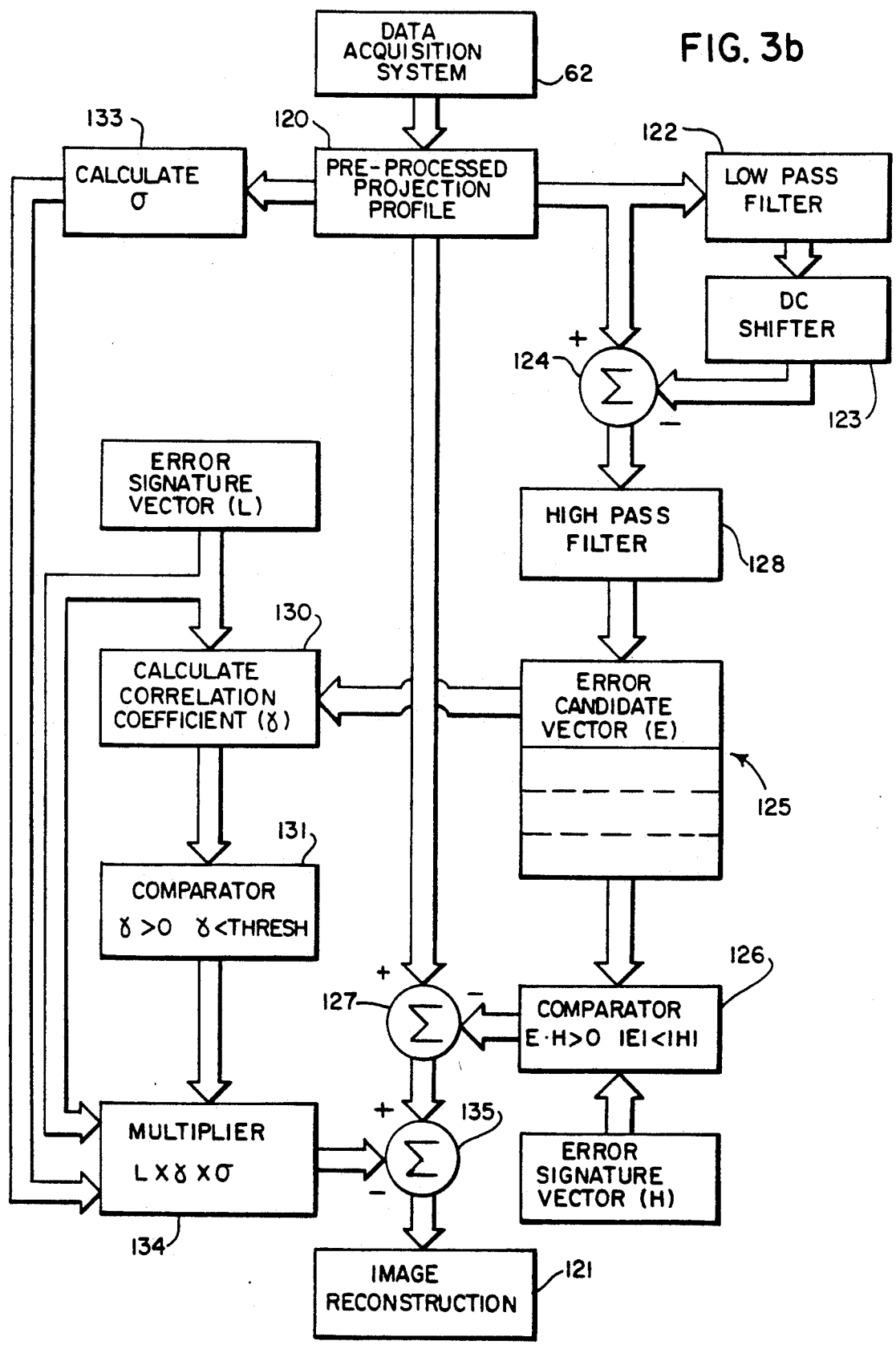
FIG. 3(b) is a block diagram showing the correction of the scan data acquired by the CT system of FIG. 2 according to the present invention.
Figure 4A:
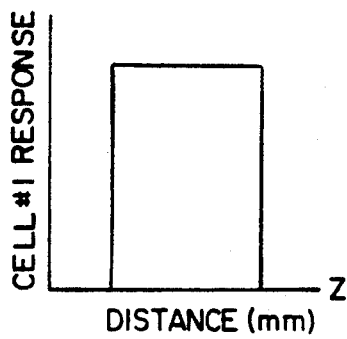
FIGS. 4(a)-(c) are graphic representations of three different z-axis sensitivity profiles of detectors used in the system of FIG. 1(a)
Figure 4B:
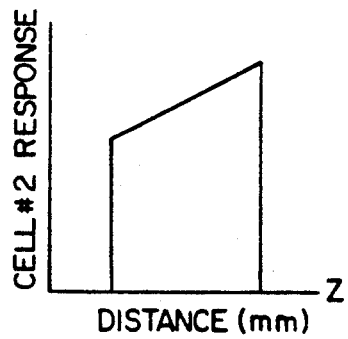
Figure 4C:
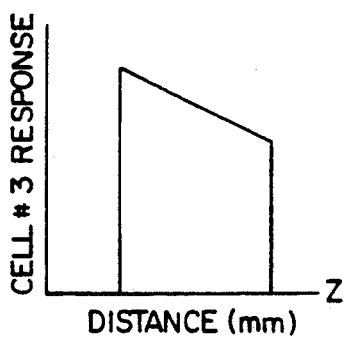
Figure 5A:
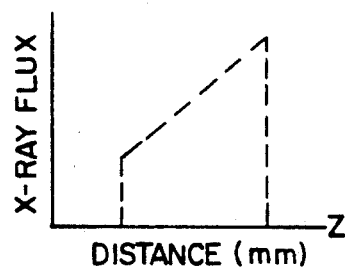
FIG. 5(a) is an exemplary x-ray flux density profile.
Figure 5B:
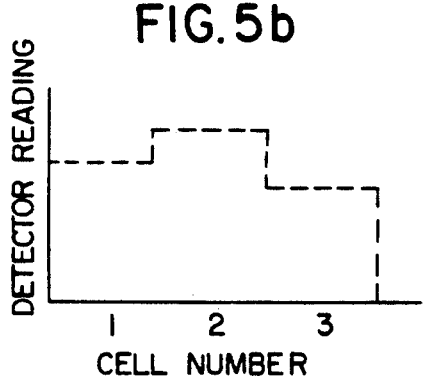
FIG. 5(b) is the resulting signals after air calibration produced by the detectors of FIGS. 4(a)-(c)
Figure 6A:
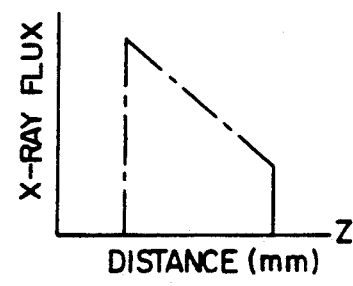
FIG. 6(a) is a second exemplary x-ray flux density profile.
Figure 6B:
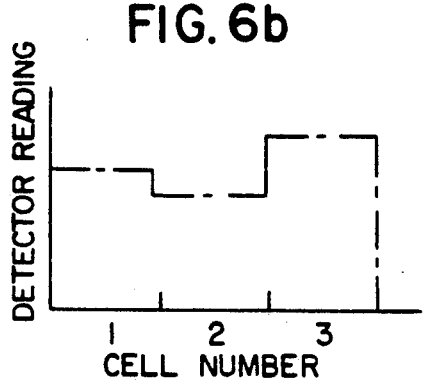
FIG. 6(b) is the resulting signals after air calibration produced produced by the detectors of FIGS. 4(a)-(c)

Referring particularly to FIG. 3(b), the image reconstructor 68 is modified to correct the fully preprocessed projection profiles as they are received at memory block 120 from the data acquisition system 62. Each projection profile is one view which includes separate values for each of the 852 detector elements that have been preprocessed to compensate for differences in channel gain, detector offsets, beam hardening, etc. Only the central 180 values in the projection profile are corrected in accordance with the preferred embodiment of the present invention, the remaining values are passed through unaltered to the image reconstruction process 121. The objective is to identify fluctuations in the central 180 detector element values that are caused by non-uniform z-axis response and apply a corrective value. If the detected "fluctuation" in the projection profile data "matches" the error vector signature (L) or (H), one can assume that the fluctuation is an error to be corrected. On the other hand, if the fluctuation in the projection profile data does not match the error vector signatures (L) or (H), the fluctuation is presumed to be either a result of the patient being imaged, statistical fluctuation of the photon noise, or errors due to other sources.

Referring still to FIG. 3(b), the first step is to separate variations in the projection data due to the structures that belong in the patient being scanned. This is accomplished by passing the central 180 channels through a low pass filter 122. The low pass filter is designed such that all the high frequency fluctuations due to z-axis errors are filtered out and the main structures of the object are preserved. A 13 point box car filter is used for this purpose. To avoid a DC shift in the filtered data, the entire projection is shifted at 123 by an amount so that the central 36 channels have the same average value as the central 36 channels of the unfiltered projection profile. The filtered output of the shifter 123 is then subtracted from the central 180 channels of the original projection data at summing point 124 to produce a 180 element vector that is input to a high pass filter 128. The high pass filter 128 is implemented by passing a copy of the input vector through a 13 point low pass Gausian filter and subtracting the result from the input vector. The resulting error candidate vector (E) embodies the fluctuations in the central 180 channels of the projection profile data that are likely to be caused by non-uniform detector element z-axis response. This vector (E) is stored in a memory 125 which contains the error candidate vectors for several (e.g. three) previously processed projection profiles.

As indicated previously, the lower frequency errors that manifest themselves as band artifacts in the image are handled separately from the higher frequency errors that manifest themselves as ring artifacts. The error candidate vector (E) is thus separately used to identify these two types of errors in the current projection profile. This is accomplished in part by a comparator 126 which compares each element of the error candidate vector (E) with the corresponding element in the high frequency error signature (H). If both elements have the same sign (E·H>0) and the error candidate fluctuation is less than the error signature fluctuation ($|E|<|H|$), then a correction may be required. But first, the same comparisons are made with the three previous error candidate vectors stored in the memory 125 to insure the fluctuation is not simply random noise. If the same conditions test true for the three previous error candidate vectors, the current error candidate vector value is subtracted from the corresponding detector channel signal in the projection profile data at a summing point 127. The corrections are thus made to the central 180 channels using the error candidate vector values (E), but the decision as to whether a correction is proper is determined by comparison with the downloaded high frequency error signature vector (H).

Referring still to FIG. 3b, correction for lower frequency, band artifacts is performed only on the central 36 detector channels where they are most disturbing in the reconstructed image. Due to the nature of the back projection image reconstruction technique, minor fluctuations in detector z-axis sensitivity have a greater impact on the center of the image. For the same reasons, however, great care must be taken in modifying these central channels to insure that errors are being corrected, not introduced.

The first step is a correlation calculation at process block 130 between the central 36 elements of the error candidate vector (E) and the low frequency error signature vector (L). This correlation indicates the degree of similarity between these two vectors and it produces a correlation factor $\gamma$ according to the following:

$$\gamma = \frac{E \cdot L}{\Sigma L^2}$$

where:

E·L = the vector dot product; and
$\Sigma L^2$ = the sum of the squares of the vector L elements.

The correlation factor $\gamma$ is then examined at comparator 131 to determine if there is a positive correlation, and if so, if the weighting factor is less than a preset threshold value. If the correlation factor $\gamma$ is negative there is no correlation between the error candidate and the signature for band artifacts and no correction is made (i.e. $\gamma$ is set to zero). Similarly, of $\gamma$ is too large the low frequency fluctuations in the error candidate vector (E) is most probably due to the structures being scanned and no correction should be made.

Figure 10:
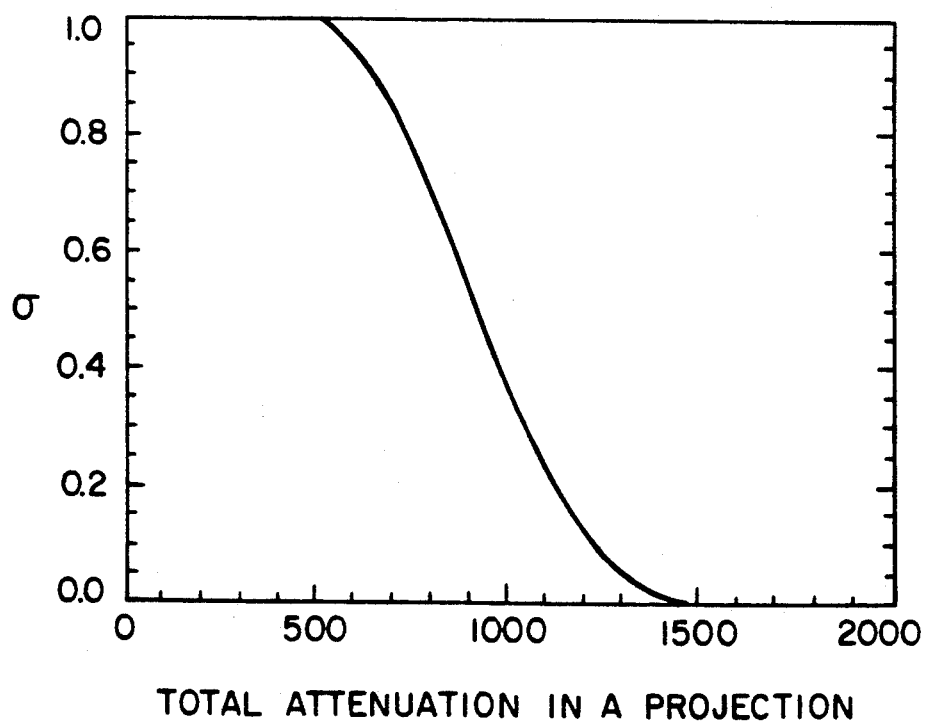
FIG. 10 is a graphic representation of a scalar value $\sigma$ employed in the process of FIG. 3(b).

To further guard against over-correction, a scalar value $\sigma$ is calculated at process block 133 using the attenuation values in the projection profile 120. The value $\sigma$ is determined by calculating the total attenuation of the projection profile and reading out a value of $\sigma$ from a stored table. For a head scan, for example, the values of this table are shown in FIG. 10. They are empirically derived and reflect the fact that in a head scan the artifacts will be greatest where the scull is sloped with respect to the plane of the fan beam—that is, where the cross section of the head is smaller and the total attenuation is less. It need only be calculated once per image and it is applied to a process block 134 which multiplies each element of the low frequency signature vector (L) by both the scalar value $\sigma$ for that image and the correlation factor $\gamma$ for this projection profile. The resulting 36 values are subtracted at summing point 135 from the central channels of the projection profile data.

Each projection profile (P) acquired during the scan is thus corrected for ring artifacts using error data (E) derived from the projection data and it is corrected for band artifacts using the previously calculated low frequency error signature data (L). The previously calculated high frequency signature data (H) is used to determine if ring artifact corrections should be made and the error data (E) derived from the projection data (P) is used to determine if the band artifact corrections should be made.

Many variations are possible from the preferred embodiment described above. There is nothing critical about the number of central channels selected for correction. The number chosen was a compromise that takes into consideration the increased processing time required when larger numbers of channels are corrected.

I claim:

1. A method for correcting x-ray data for a computed tomography system having an x-ray source for producing a fan beam of x-rays along a fan beam plane and with a thickness in a direction normal to the fan beam plane, and having a set of detector elements disposed in the fan beam of x-rays to produce a corresponding set of attenuation signals that indicate the x-ray flux density profile of the fan beam, the steps comprising:

acquiring a set of attenuation signals from the detector elements with a reference phantom disposed in the fan beam of x-rays that attenuates the x-rays such that the flux density of the x-rays striking the detector elements has a substantial gradient along the thickness direction;

filtering the acquired set of attenuation signals to produce an error signature vector having elements whose values are indicative of variations in the response of detector elements along the thickness direction;

acquiring sets of attenuation signals from the detector elements with a subject to be imaged disposed in the fan beam of x-rays and correcting each set of attenuation signals prior to reconstructing an image by:

a) producing an error candidate vector from said set of attenuation signals by filtering therefrom variations in the attenuation signals caused substantially by structures in the subject to be imaged;

b) comparing the error signature vector with the error candidate vector to identify specific attenuation signals in the set of attenuation signals that require correction; and c) correcting the identified attenuation signals.

2. The method as recited in claim 1 in which the correction of identified attenuation signals is performed using values from said error candidate vector.

3. The method as recited in claim 1 in which the correction of identified attenuation signals is performed using values from the error signature vector.

4. The method as recited in claim 3 in which the correction of identified attenuation signals is also performed using values from the error candidate vector.

5. The method as recited in claim 1 in which the reference phantom is a rod that has its lengthwise dimension disposed in the plane of the fan beam and which is constructed to variably attenuate x-rays along the thickness direction.

6. The method as recited in claim 5 in which the rod is tapered.

7. The method as recited in claim 1 in which the reference phantom is a circular disc disposed in the plane of the fan beam and the error signature vector is produced by averaging corresponding values in a plurality of sets of attenuation signals acquired by passing the fan beam of x-rays through the circular disc from a corresponding plurality of different angles.

8. The method as recited in claim 7 in which the circular edge of the circular disc is tapered.

* * * * *